(12) United States Patent
Shinden

(10) Patent No.: US 7,699,523 B2
(45) Date of Patent: Apr. 20, 2010

(54) RADIATION IMAGE PHOTOGRAPHING APPARATUS

(75) Inventor: Yuko Shinden, Hino (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 5 days.

(21) Appl. No.: 11/764,897

(22) Filed: Jun. 19, 2007

(65) Prior Publication Data
US 2007/0297563 A1  Dec. 27, 2007

(30) Foreign Application Priority Data
Jun. 23, 2006 (JP) .............. 2006-174114
Oct. 6, 2006 (JP) .............. 2006-275503

(51) Int. Cl.
*A61B 6/04* (2006.01)
(52) U.S. Cl. ...................................... 378/208
(58) Field of Classification Search ............ 378/162, 378/165, 195, 196, 208
See application file for complete search history.

(56) References Cited

U.S. PATENT DOCUMENTS 3,609,355 A * 9/1971 Schwarzer ............ 378/37
5,640,438 A * 6/1997 Talluto et al. ........... 378/165
2004/0161075 A1 * 8/2004 Amitani ................ 378/37
2006/0039532 A1 * 2/2006 Wu et al. ............... 378/62
2007/0076938 A1 * 4/2007 Hartman et al. ......... 382/132

FOREIGN PATENT DOCUMENTS

| EP | 0524063 | 1/1993 |
|---|---|---|
| JP | 2004173879 | 6/2004 |
| JP | 2005040505 | 2/2005 |

* cited by examiner

*Primary Examiner*—Chih-Cheng G Kao
(74) *Attorney, Agent, or Firm*—Lucas & Mercanti, LLP

(57) ABSTRACT

Radiation image photographing apparatus equipped with radiation source irradiating subject with radiation, detector holding part holding radiation image detector that detects radiation that is emitted from radiation source and is transmitted through subject, subject table that is arranged between the radiation source and detector holding part and holds subject, and with holding device that holds the radiation source, the subject table and the detector holding part so that phase contrast image may be generated, wherein an edge portion of the subject table is protruded toward the opposite side of the holding device beyond the edge portion of the detector holding part.

17 Claims, 9 Drawing Sheets

RADIATION IMAGE PHOTOGRAPHING APPARATUS

This application is based on Japanese Patent Applications No. 2006-174114 filed on Jun. 23, 2006 and No. 2006-275503 filed on Oct. 6, 2006 in Japanese Patent Office, the entire content of which is hereby incorporated by reference.

BACKGROUND OF THE INVENTION

The present invention is related to a radiation image photographing apparatus, and in particular, to a radiation image photographing apparatus for taking a radiation image for diagnosing deformation of joints.

Heretofore, an examinee has needed to be fixed in the course of taking a radiation image, and, for example, there is known an apparatus to press and fix an abdominal region of an examinee with an air pillow when radiographing a digestive organ which is shown in Patent Document 1. Further, in the case of a breast-radiographing apparatus, a compression board is usually used to fix a subject on a subject table.

As shown in FIG. 13, the breast-radiographing apparatus 50 of this kind is provided with radiation source 51 that irradiates radiation toward subject H, detector holding device 52 that holds a radiation image detector detecting radiation that is emitted from radiation source 51 and is transmitted through subject H, and with subject table 53 that is arranged between the radiation source 51 and the detector holding device 52 to hold the subject H. These constituting structures are provided vertically, so that an examinee may be radiographed while keeping an upright posture.

There is further known a radiation image photographing apparatus to take a phase contrast image for improving sufficiently the contrast of a radiation image to be obtained (for example, see Patent Document 2). When taking a phase contrast image, it is necessary to provide a distance in prescribed quantity between radiation source 51 and a subject and between a subject and a radiation image detector. The phase contrast photographing of this kind is one of magnification techniques.

Now, a rheumatism disease is given as one of diseases appearing on the limbs. The rheumatism disease includes a symptom appearing on a bone region such as osteoporosis and a symptom appearing on a cartilage region such as cartilage destruction. Since these symptoms appear earliest on a cartilage region of the limbs, images obtained through photographing of a cartilage of fingers by MRI have been used for diagnoses. However, the photographing by MRI causes a heavy burden for an examinee from the viewpoint of expenses and time required for diagnoses, resulting in a problem that periodical photographing and observation of changes in a cartilage of fingers are difficult.

Recently, therefore, the inventors of the present invention has suggested a technology which can capture images of cartilage portions which are highly visible through taking phase contrast images by using a X-ray photographing apparatus, even in the case where X-ray absorbing difference is small as in the space between the cartilage region and its periphery. The invention in this case provides a radiation image photographing apparatus that generates highly visible images of a joint region including a cartilage region.

In the radiation image photographing apparatus of the invention, it is possible to radiograph periodically a joint region of fingers of an examinee, and thereby, it is easy to conduct observation diagnoses for presence or absence of aging changes of cartilage of a joint region (for example, wearing-off of a cartilage region or the like), thus, it is possible to subdue disease spreading by early detection of rheumatism diseases and by early medical treatment for patients.

In conventional radiation image photographing apparatus 50, there has been a problem that detector holding device 52 is protruded toward the examinee side from an edge of subject table 53, thereby, a posture to approach the subject table 53 cannot be taken and the arm of the examinee is not stabilized, making it difficult to fix fingers. However, the radiation image photographing apparatus of the present invention makes it possible to solve the aforesaid problem. Therefore, even if an examinee is relatively old in terms of an age, motion artifact of the arm is hardly caused, and it is easy to radiograph without movement of fingers, which does not force a burden on the examinee. Further, even if an extent of opening and the direction of fingers of the examinee are different in each radiographing, an irradiation angle of radiation for the subject can be made constant, thereby, it is possible to detect aging changes by comparison of finger radiographic images, even if the aging changes are slight.

[Patent Document 1] Japanese Patent Publication Open to Public Inspection No. 2005-40505

[Patent Document 2] Japanese Patent Publication Open to Public Inspection No. 2004-173879

SUMMARY

To solve the aforesaid problems, an embodiment of the invention is characterized, in the radiation image photographing apparatus which is provided with a radiation source that irradiates a radiation on a part of an examinee representing a subject, a detector holding device that holds a radiation image detector that detects the radiation that is emitted from the radiation source and is transmitted through the subject and with a subject table that is arranged between the radiation source and the detector holding device and holds the subject, so that phase contrast images may be generated, by the aforesaid subject table that is protruded toward the examinee side beyond an edge of the detector holding device.

DETAILED DESCRIPTION OF THE PREFERRED EMBODIMENT

Figure 1:
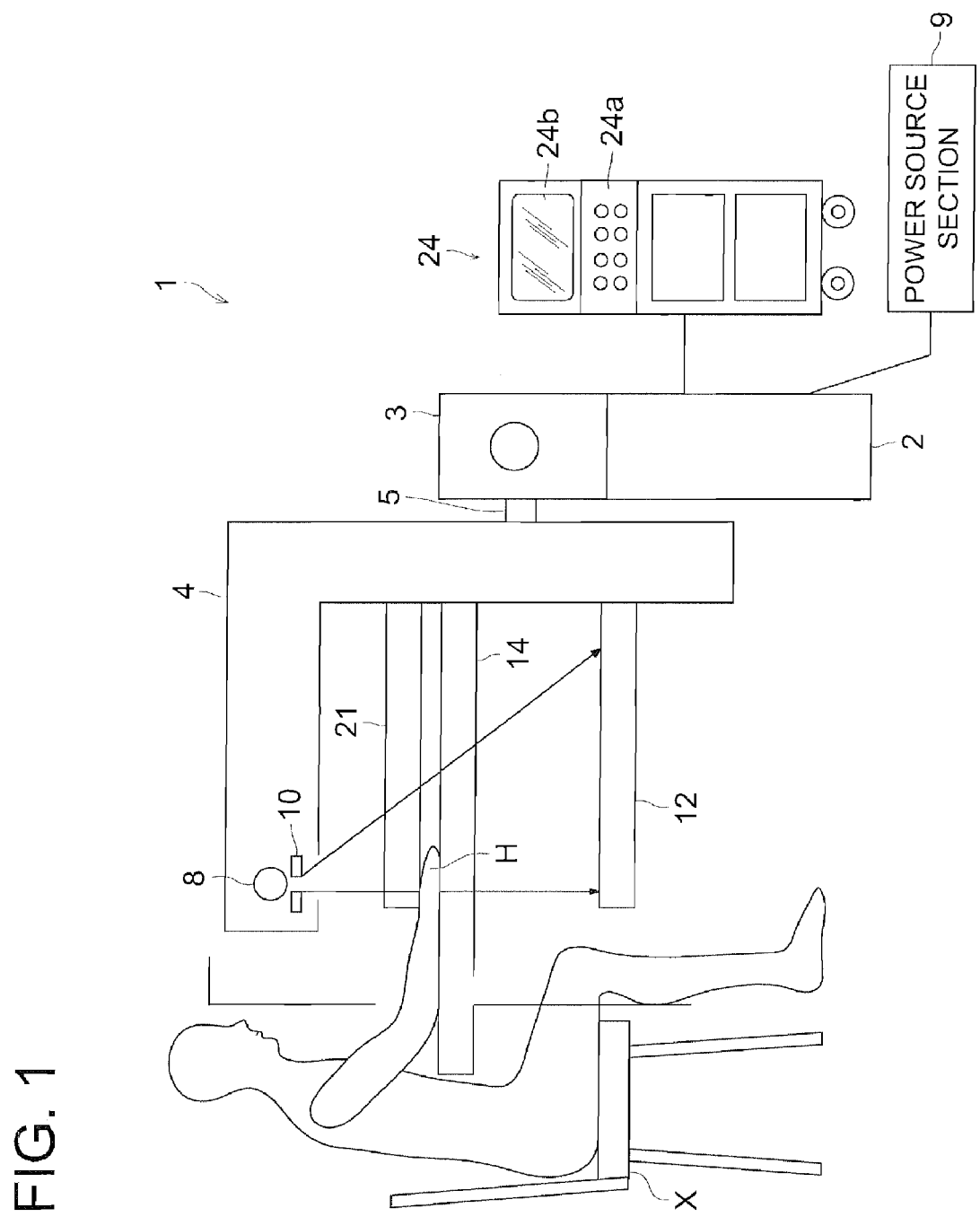
FIG. 1 is a side view showing the main structures of the radiation image photographing apparatus in the invention.

In the embodiment of the invention, an examinee can approach a radiation image photographing apparatus and can take a comfortable posture by placing fingers and an arm portion below an elbow on a subject table, because the subject table is protruded toward the examinee side beyond an edge portion of a detector holding device. Under the circumstances where the fingers of the examinee are fixed in the aforesaid way, the radiation emitted from the radiation source is transmitted through the fingers of the examinee representing a subject on the subject table, and it enters a radiation image detector held by the detector holding device. The radiation image detector generates phase contrast images based on the radiation which has entered the radiation image detector.

The embodiment of the invention is characterized in that the relative positions between the radiation source and the detector holding device are fixed, and the relative position of the subject table can be changed in the radiation image photographing apparatus described above.

In this embodiment of the invention where the relative positions between the radiation source and the detector holding device are fixed, an enlargement ratio in the phase contrast image can be adjusted while keeping a distance from the radiation source to the detector holding device (which is an apparatus height) to be constant, by changing the relative position of the subject table.

The embodiment of the invention is characterized in that a discriminating device for right and left that determines whether the aforesaid subject held on the subject table is a left hand or a right hand, is provided in the radiation image photographing apparatuses described above.

In this embodiment of the invention, the discriminating device for right and left determines whether the hand of the examinee held on the subject table is a left hand or a right hand, and a joint region of the fingers is radiographed in the prescribed direction.

The embodiment of the invention is characterized in that a discriminating device for the radiographing direction that determines the orientation of the subject held on the subject table is provided in the radiation image photographing apparatuses described above.

In this embodiment of the invention, the discriminating device for the radiographing direction determines which of the back of the hand and the palm faces upward about a hand of the examinee held on the subject table. Then, a joint region of the fingers is radiographed in the prescribed direction based on the discerned radiographing direction.

The embodiment of the invention is characterized in that an image data generating section that generates image data of the aforesaid phase contrast images and an information supplementing device that causes information for right and left by the aforesaid discriminating device for right and left and/or information of radiographing direction by the discriminating device for the radiographing direction to be attached to the image data, are provided in the radiation image photographing apparatuses described above.

In the embodiment of the invention, information for right and left by the discriminating device for right and left and/or information of radiographing direction by the discriminating device for the radiographing direction are transmitted to the information supplementing device, and then, the information supplementing device causes these attached pieces of information to be correlated to image data generated by the image data generating section.

An example of the radiation image photographing apparatus relating to the invention will be explained as follows, referring to the drawings. However, the scope of the invention is not limited to the illustrated examples.

FIG. 1 shows a structural example of radiation image photographing apparatus 1 in the present embodiment. On the radiation image photographing apparatus 1, supporting base 3 is provided on radiographing apparatus main body part 4 representing a base, in a way to be capable of rising and lowering freely relative to supporting pedestal 2. On the supporting base 3, the radiographing apparatus main body part 4 which is substantially in a shape of a rectangular parallelopiped is supported through supporting shaft 5 so that the radiographing apparatus main body part 4 may be rotated freely in the CW (clockwise) direction and in the CCW (counter clockwise) direction. The supporting base 3 is provided with drive device 6 that drives rising and lowering of the supporting base 3 and rotation of the supporting shaft 5. The drive device 6 is provided with an unillustrated known drive motor and others. The supporting base 3 and the radiographing apparatus main body part 4 are arranged to rise and lower depending on the position of subject H. The position of the subject H means a position in the vicinity of a shoulder of an examinee sitting on a chair X, and it can be adjusted to the position which allows an examinee to place an arm on subject table 14 described later and to take a posture in which the examinee hardly becomes fatigued.

Figure 2:
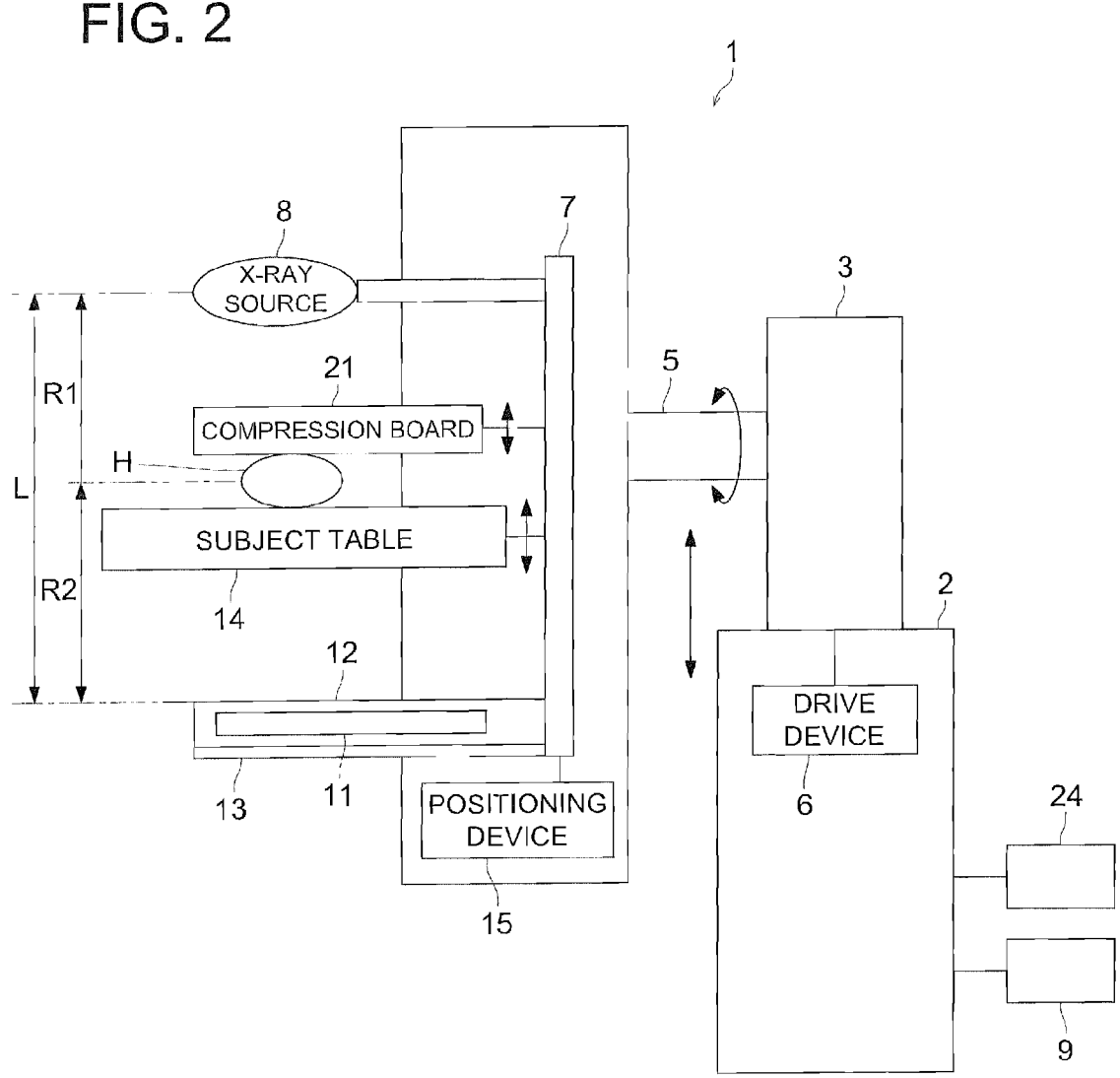
FIG. 2 is a schematic diagram showing internal structures of the radiation image photographing apparatus in the invention.

As shown in FIG. 2, holding member 7 is provided in the vertical direction in the radiographing apparatus main body part 4. On the upper part of the holding member 7, there is attached X-ray source 8 representing a radiation source that emits radiation on subject H. To the X-ray source 8, there is connected power source section 9 that applies tube voltage and tube current, through supporting shaft 5, supporting base 3 and radiographing apparatus main body part 4. Diaphragm 10 that adjusts radiation irradiation field is provided on a radiation aperture of the X-ray source 8 on a way to open and close freely.

As the X-ray source 8, it is preferable that a rotating anode X-ray tube is used. In this rotating anode X-ray tube, X-ray is generated when an electron beam emitted from a cathode collides against an anode. This is incoherent, which is the same as natural light, and is divergent light without being parallel light X-ray. When the electron beam keeps hitting the fixed location on the anode, the anode is damaged by generated heat. Thus, in the X-ray tube used usually, the anode is rotated to prevent a decline of a life of the anode. An electron beam is caused to hit the surface in a certain area on the anode, and X-ray generated is emitted to subject H from the flat surface in the same size on the anode. This flat surface is called a focus. Focus size D (μm) means a length of one side of a square when the focus is in a form of the square, while, it means a length of a shorter side of a rectangle or of a polygon when the focus is in a form of the rectangle or the polygon and it means a diameter of a circle when the focus is in a form of the circle. When the focus size D is greater, a dose of radiation to be emitted is larger.

On the lower part of holding member 7, there is fixed one end of detector holding part 12 that holds radiation image detector 11 which detects the radiation transmitted through subject H. As the radiation image detector 11, there are given, for example, a cassette that houses a stimulable phosphor sheet, a screen (intensifying screen)/film and FPD (flat panel detector). In the present embodiment, the radiation image detector 11 whose size is 14×17 (inches) is used. Further, a relative position between X-ray source 8 and detector holding part 12 is fixed, and its distance is assumed to be represented by L.

Radiation dose detecting section 13 that detects a dose of emitted radiation is provided on the bottom surface of the detector holding part 12 at the lower part of the holding member 7.

Between the X-ray source 8 and the detector holding part 12, there is provided flat-plate-shaped subject table 14 that holds examinee's fingers representing subject H from underneath, with its one end being fitted on the holding member 7. The subject table 14 is connected with positioning device 15 that is equipped with a motor for changing a position relative to the holding member 7, for adjustment of shooting magnification (adjustment of a position in the direction of a height) in the case of phase contrast radiographing.

The subject table 14 is formed to be protruded toward the examinee side beyond the other edge of the detector holding part 12. Overt the subject table 14, there is provided compression board 21 that presses and fixes subject H from above, with its one end being fitted on the holding member 7. The compression board 21 can move freely along the holding member 7, while keeping its posture to be in parallel with the subject table 14. Any of automatic movement and manual movement can be applied to the movement of the compression board 21. An edge of the compression board 21 is arranged to be protruded slightly toward the examinee side beyond the X-ray source 8 and the radiation image detector 11 (edge of effective image) which are arranged substantially vertically. Therefore, if a range of a target object to be radiographed (for example, a right hand) of an examinee is arranged to be closer to the holding member 7 than the compression board 21 is, image missing for an area of interest (a range to be radiographed) is not caused, which is preferable. It is further preferable that an edge of subject table 14 is made to be in a form of curved surface and an aged examinee having an average figure can lean its upper half of the body over the subject table 14 when the examinee sits on chair X. In that case, the examinee can be positioned at a radiographing location without hitting the detector holding part 12 with his or her leg under the condition of sitting on chair X.

Figure 3:
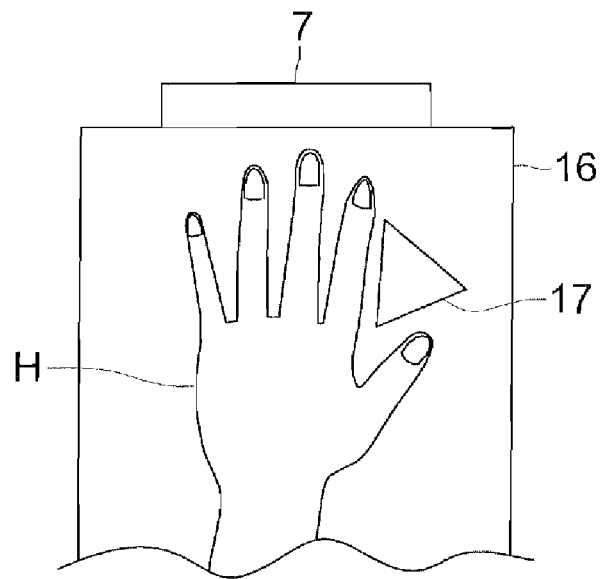
FIG. 3 is a top view wherein an examinee places his or her left hand on a hand-holding member in the invention, with the back of the hand facing upward.
Figure 4:
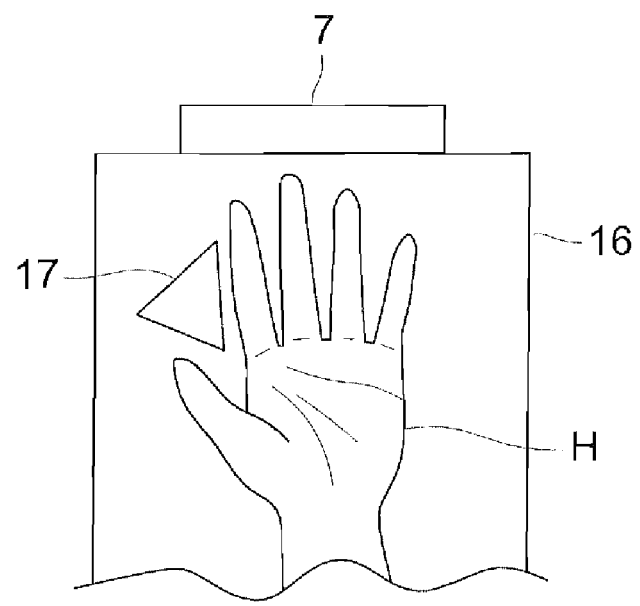
FIG. 4 is a top view wherein an examinee places his or her left hand on a hand-holding member in the invention, with the palm of the hand facing upward.

As shown in FIG. 3 and FIG. 4, hand-holding member 16 that holds the fingers of an examinee is provided on the subject table 14 to intersect with a radiation irradiation path. A size of the hand-holding member 16 is not limited in particular, provided that fingers of an examinee can be placed. On the upper surface of the hand-holding member 16, there is provided triangle magnet 17 that is arranged between the thumb and a forefinger when an examinee places fingers on the hand-holding member 16. On the hand-holding member 16, there is provided radiographing direction discriminating device 18 (see FIG. 7) that detects a location where triangle magnet 17 is placed and discriminates a position of the thumb of the examinee as the radiographing direction information.

Figure 5:
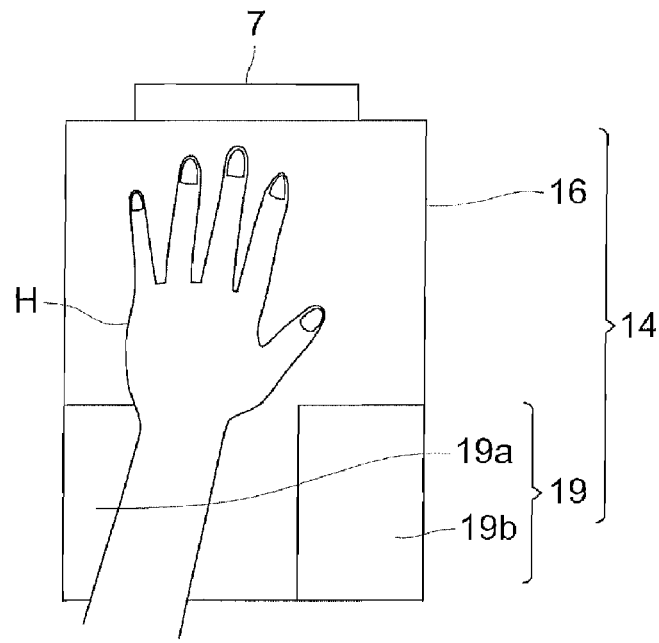
FIG. 5 is a top view wherein an examinee places his or her left hand on a subject table in the invention.
Figure 6:
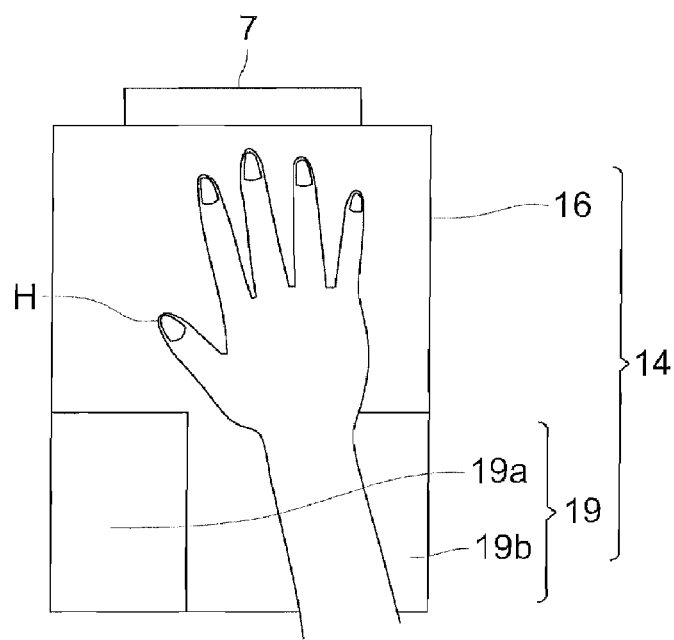
FIG. 6 is a top view wherein an examinee places his or her right hand on a subject table in the invention.

As shown in FIG. 5 and FIG. 6, arm-holding member 19 that holds an arm of an examinee is provided on the position that is closer to the examinee side than the hand-holding member 16 of the subject table 14 is. On the arm-holding member 19, there are provided left-arm-holding member 19a and right-arm-holding member 19b, and the examinee can place either a left arm or a right arm depending on photographing conditions. A size of the arm-holding member 19 is not limited in particular, and the examinee can fix its fingers stably and sufficiently if the arm below an elbow of the examinee can be placed. On each of the left-arm-holding member 19a and the right-arm-holding member 19b, there is provided weight sensor 20 (see FIG. 7) as a discriminating device for right and left that determines a right hand or a left hand of the examinee (information about right and left) depending on which one of the left-arm-holding member 19a and the right-arm-holding member 19b the arm portion of the examinee is placed on. With respect to the weight sensor 20, those which are widely known can be used without any restriction, and the number of weight sensors 20 and installation positions for them are not restricted in particular.

Radiographing direction information acquired by the radiographing direction discriminating device 18 and information for right and left acquired by weight sensor 20 are outputted to information supplementing device 26 through control device 22 which will be described later. The information supplementing device 26 may also correlate radiographing direction information and/or information for right and left to image data of phase contrast images to be generated as supplementary information. Supplementary information is not limited to those mentioned above, and ID information of an examinee may also be supplemented.

Figure 7:
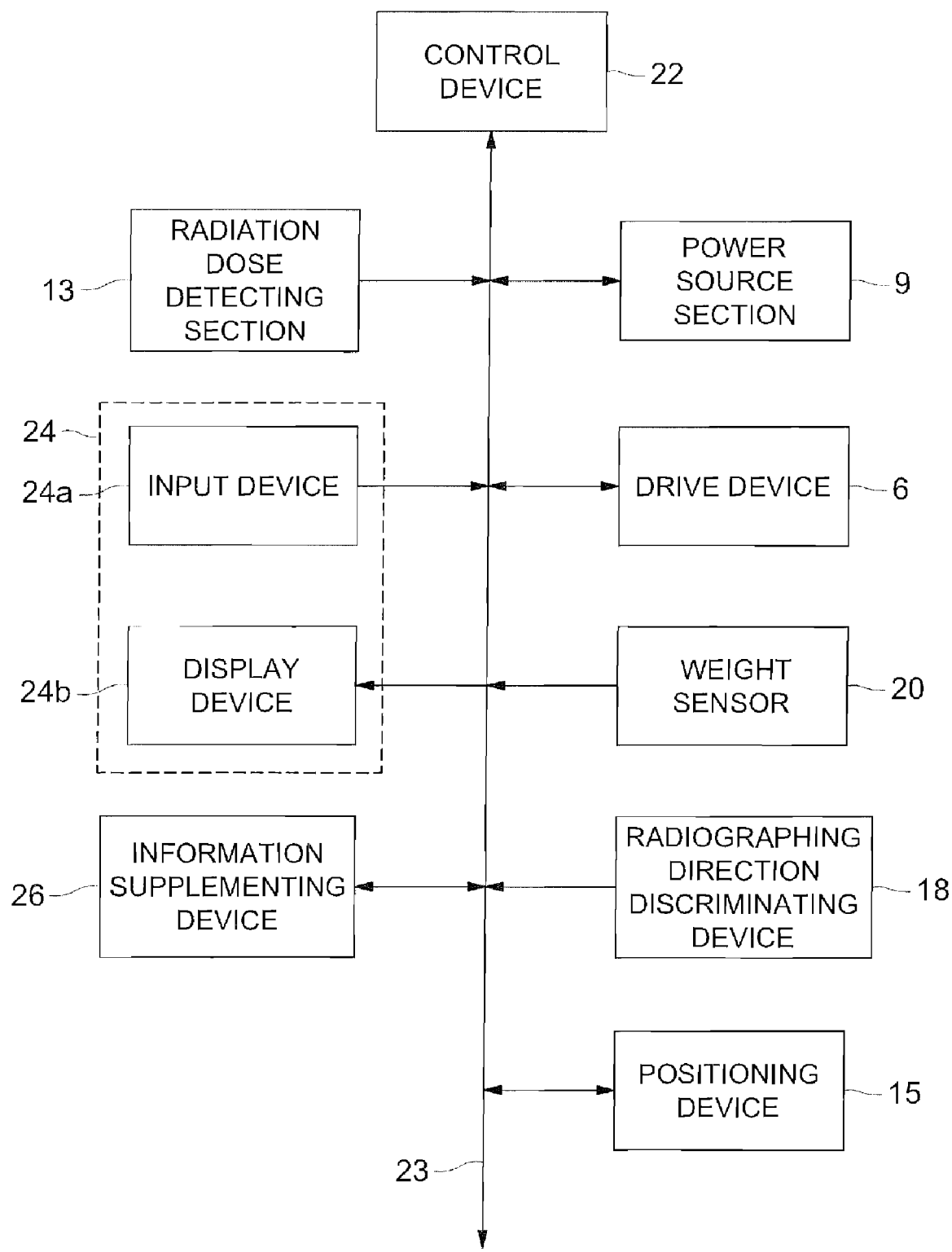
FIG. 7 is a block diagram showing a control mechanism of the radiation image photographing apparatus in the invention.

As shown in FIG. 7, radiographing apparatus main body part 4 is equipped with control device 22 that is composed of CPU (Central Processing Unit), ROM (Read only Memory) and RAM (Random Access Memory). Radiation dose detecting section 13, power source section 9, drive device 6, positioning device 15, weight sensor 20, information supplementing device 26 and radiographing direction discriminating device 18 are connected to the control device 22 through bus 23. Further, operation device 24 having input apparatus 24a equipped with a key board and touch panel (not shown) which conduct input of radiographing conditions and a position adjusting switch for adjusting a position of subject table 14 and display device 24b such as CRT display and a liquid crystal display are connected to the control device 22. In the ROM of the control device 22, there are stored control programs and various processing programs for controlling respective parts of radiation image photographing apparatus 1, and CPU controls generally operations of respective parts of the radiation image photographing apparatus 1 through cooperation with the control programs and various processing programs, then, conducts phase contrast radiographing and functions as an image data generating section that generates image data of the phase contrast images.

For example, CPU controls drive device 6 based on results of the discrimination by weight sensor 20 and radiographing direction discriminating device 18 and on radiographing conditions for an examinee, then, causes radiographing apparatus main body part 4 to rise and lower to the height adjusted to the examinee's height, and rotates supporting shaft 5 for adjusting an irradiation angle of radiation. Then, it adjusts a position of subject table 14 by positioning device 15, and adjusts a magnification rate of phase contrast radiographing. After that, the radiographing apparatus main body part 4 conducts radiographing processing, by causing power source section 9 to apply tube voltage and tube current on X-ray source 8 to irradiate subject H with radiation, and when a dose of radiation inputted from the radiation dose detecting section 13 arrives at the dose of radiation set in advance, it causes power source section 9 to stop irradiation of radiation from X-ray source 8.

Figure 8:
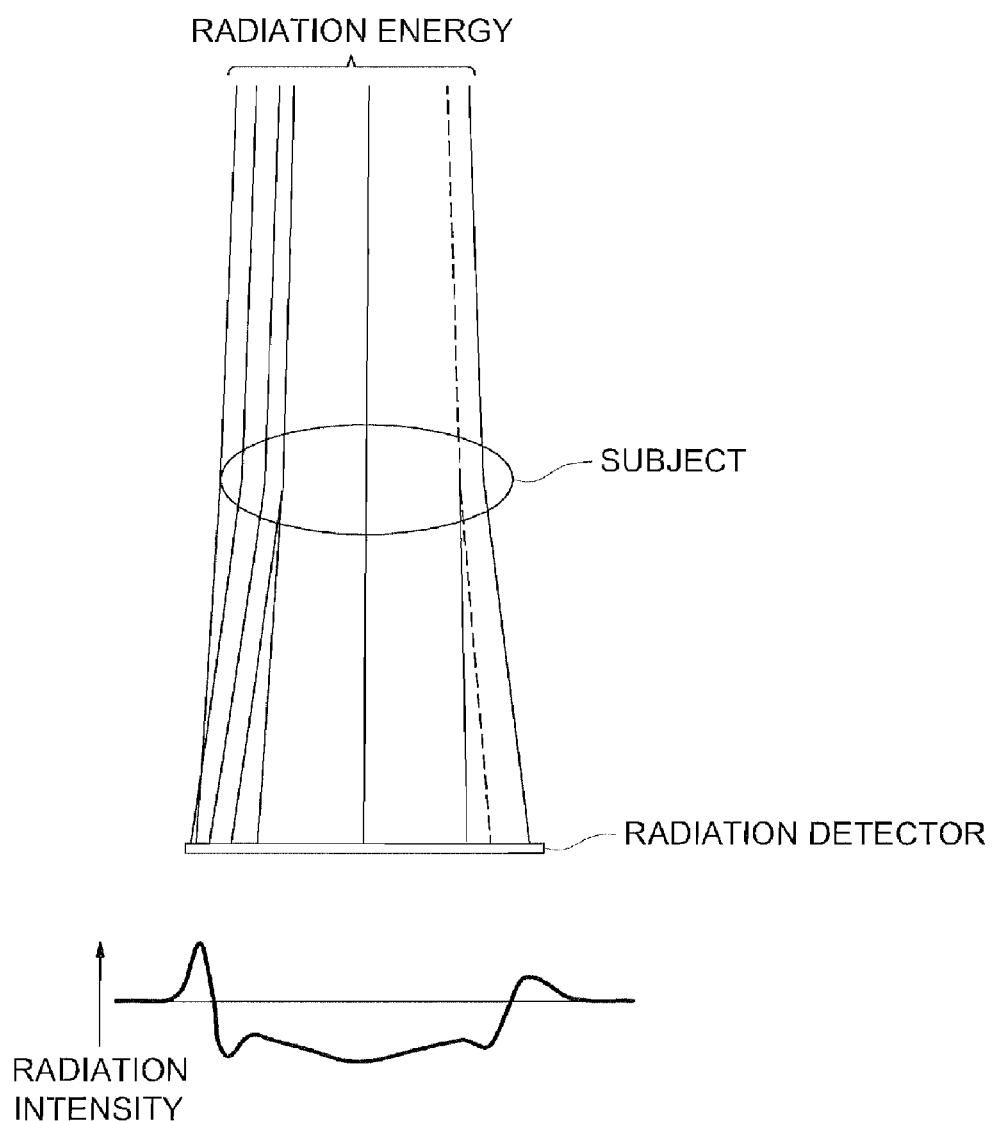
FIG. 8 is an illustration showing a principle of phase contrast radiographing.

Now, a principle of phase contrast radiographing will be explained as follows, referring to FIG. 8. The phase contrast radiographing is a radiographing in which an edge-emphasized (refraction-contrast-enhanced) image caused by refraction of radiation is obtained as shown in FIG. 8 by providing certain distance R2 between subject H and radiation image detector 11. As is drawn schematically in FIG. 8, when a radiation is transmitted through an object, the radiation density is lowered by refraction on the inside of boundary of the object, while, the radiation density is enhanced further on the outside of the object because of overlapping of the radiation with other radiation which is not transmitted through the object. Thus, an edge representing a boundary portion with a subject is emphasized as an image. This is a phenomenon caused by a difference of the refractive index for radiation between an object and air. This is an edge-emphasized image.

Further, the same effect can be obtained not only for edge-emphasis at the boundary between air and a subject as shown in FIG. 8 on a principle basis but also for a boundary portion between sections each having a different refractive index in an object. The subject boundary portion in the present invention can also be expressed as a boundary portion between substances each having a different refractive index for radiation.

When conducting phase contrast radiographing, it becomes enlargement radiographing at the radiographing magnification of "enlargement rate=(R1+R2)/R1", under the condition that R1 represents a distance from X-ray source 8 to subject H and R2 represents a distance between subject H and a radiation image detector. With respect to R1, its starting point is a position of the focus of the X-ray source 8, and that position is pointed out clearly on the ordinary X-ray source 8 available on the market. Incidentally, an ending point is a center line of subject H fixed by subject table 14 that fixes a subject position, and in this case, the center line of subject H is a position that is equally distant from the subject table 14 and from the compression board 21. With respect to R2, its starting point is a center line of subject H, and its ending point is an uppermost surface on a flat surface of a radiation image detector that receives a radiation, namely, the uppermost surface of detector holding part 12.

Next, operations in the present embodiment will be explained as follows.

First, an examinee places its right or left arm portion on subject table 14 based on radiographing order information, and then, triangle magnet 17 is positioned between the thumb and a forefinger.

After placing of subject H is completed, the examinee's arm portion placed on arm-holding member 19 is discriminated by weight sensor 20 whether it is a left hand or a right hand. In detailed explanation, the results of discrimination of the presence or absence of load of weight sensor 20 are outputted to control device 22. The control device 22 determines so that any of the left-arm-holding member 19a and right-arm-holding member 19b having more detections of load detected by weight sensor 20 provided on the left-arm-holding member 19a and right-arm-holding member 19b, is one on which the arm portion of the examinee is placed. The control device 22 outputs the results of the discrimination to radiographing direction discriminating device 18.

After determining whether the examinee's hand placed is a left hand or a right hand, the radiographing direction discriminating device 18 determines which of the back of the hand and the palm of the hand of the examinee placed on hand-holding member faces upward, and determines an orientation of the hand representing the radiographing direction. In detailed description, the radiographing direction discriminating device 18 determines a position of the thumb based on the position of setting of triangle magnet 17 and determines an orientation of the hand of the examinee by matching it with the results of discrimination by weight sensor 20. The results of discrimination are outputted to the control device 22, and an appropriate radiation irradiation angle is calculated. Incidentally, when there are available image data of examinee's fingers taken through radiographing in the past, information for right and left and/or information of radiographing direction as supplementary information is extracted, and when it does not agree with the setting this time, that situation may be given as a warning on display device 24b. Further, when there are not available image data of examinee's fingers taken through radiographing in the past, supplementary information may be established on control device 22 as one of radiographing order information for the examinee.

After that, adjustment of a position of subject table 14 and adjustment of an angle of radiographing apparatus main body part 4 both matching the radiographing conditions such as a radiation irradiation angle and an irradiation distance are conducted by drive device 6 and positioning device 15. After adjusting the position and angle, prescribed tube voltage and tube current are applied on X-ray source 8 by power source section 9, and subject H is irradiated with radiation emitted from X-ray source 8 for conducting radiographing. When radiographing is conducted in this way, the control device 22 generates image data of phase contrast images, and supplementary information is made by information supplementing device 26 to correspond to the image data thus generated. The generated image data are processed based on acquired supplementary information and on supplementary information in the past, to have a layout capable of being read on a comparison basis, to be displayed by display device 24b, which is preferable.

Incidentally, preferable radiographing conditions include R1=430–650 mm, R2=490–750 mm, focus size D=100 μm, tube voltage 30 kVp and tube current 30 mA. Further, an examinee causes its palm of the hand or the back of the hand to face the X-ray source 8 side in the course of radiographing, and it is preferable that the palm of the hand is turned to the X-ray source 8 side, because visibility is improved.

In radiation image photographing apparatus 1 of the present embodiment, an examinee can take comfortable posture by placing a hand and an arm portion below an elbow on subject table 14 as stated above, and therefore, it is easy for the examinee to prevent from moving fingers, which makes it possible to radiograph a cartilage region of fingers under the circumstances where fingers are fixed. Further, since the contrast between the fingers and their circumference in the radiation image obtained has been improved by phase contrast radiographing, presence or absence of aging changes of cartilage portion can be determined easily and accurately. Since it is further possible to discriminate presence or absence of aging changes of cartilage portion by using the radiation image photographing apparatus 1, it is not necessary to use a specific apparatus such as MRI, and it is possible to diagnose a rheumatic disease without placing a burden on the examinee.

By changing the position where the subject table 14 is held by holding member 7, the rate of enlargement for the phase contrast image is adjusted.

Further, by providing weight sensor 20 on arm-holding member 19, it is possible to determine whether the hand placed on the subject table 14 by the examinee is a left hand or a right hand. Further, the orientation of the hand of the examinee placed on the subject table 14 is discriminated by radiographing direction discriminating device 18, and an image is taken by radiogaphing by irradiating radiation in the direction corresponding to the aforesaid orientation, whereby, it is possible to determine aging changes easily under the fixed angle of radiographing for fingers. Further, when the examinee maintains the state wherein the thumb and a forefinger of the examinee are made to agree with triangle magnet 17 in terms of a form, a degree of opening fingers in the course of radiographing can be made constant.

Incidentally, when ID of CR cassette representing radiation image detector 11 is read by a photographing apparatus, and reading processing is conducted by moving the cassette after radiographing to the reading apparatus, the reading apparatus transmits reading image data to the control device 22 together with the cassette ID, and the control device 22 makes reading image data and supplementary information to be correlated to each other with the cassette ID serving as a key.

Further, when the radiation image detector 11 is FPD, it is possible for the control device 22 to acquire image data obtained and results of discrimination by discriminating device for right and left and by radiographing direction discriminating device 18, to make them to be correlated to each other, and to store them in a memory. On the contrary, it is possible for FPD to acquire the results of the discrimination from the control device 22 to store them as supplementary information for image data, and to transmit all data (image data and supplementary data) to an image filing device from FPD after completion of all radiographing.

Further, though weight sensor 20 was used to conduct discrimination for right and left, it is also possible to use a photosensor for conducting discrimination for right and left. In this case, the photosensor detects presence or absence of an arm portion of an examinee to conduct discrimination for right and left by irradiating light from the upper surface of arm-holding member 19 and by detecting light reflection by an arm portion of an examinee.

Figure 9:
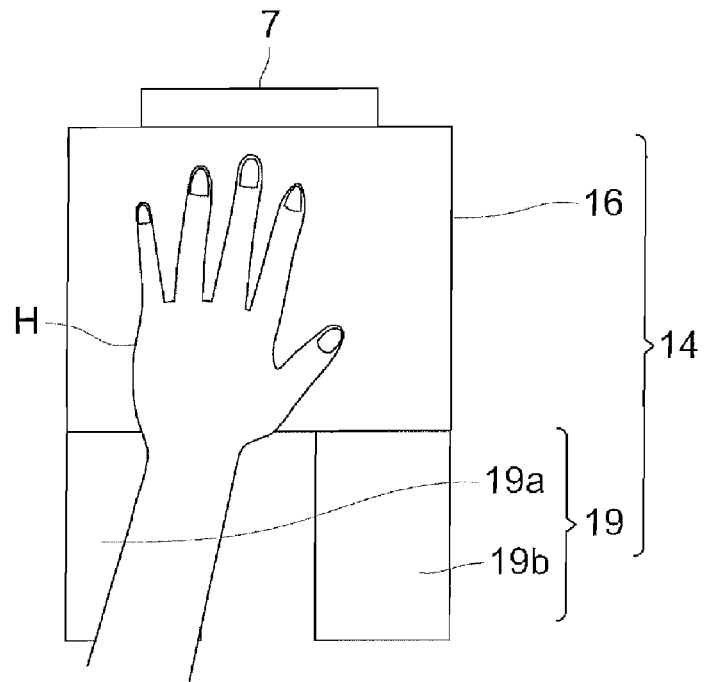
FIG. 9 is a top view showing a variation of a subject table in the invention.
Figure 10:
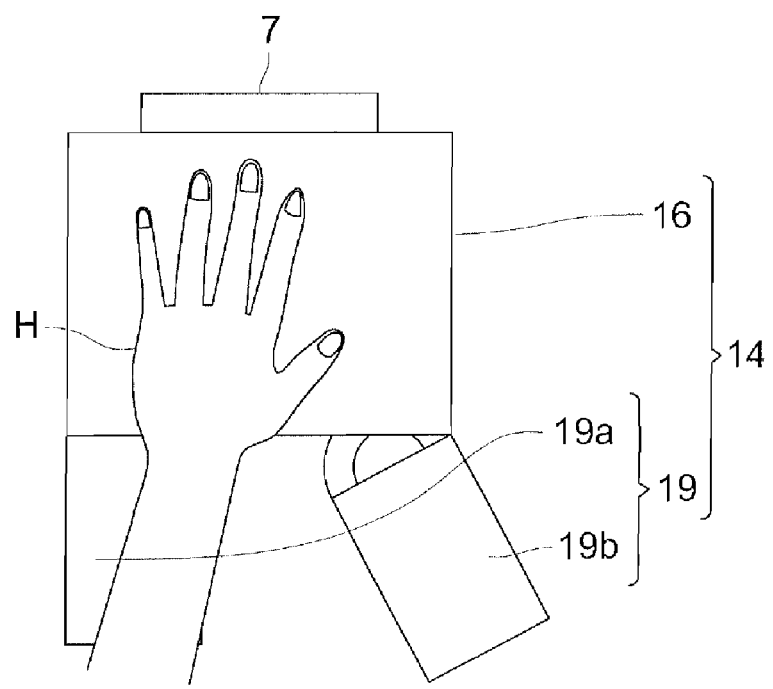
FIG. 10 is a top view showing a variation of a subject table in the invention.
Figure 11:
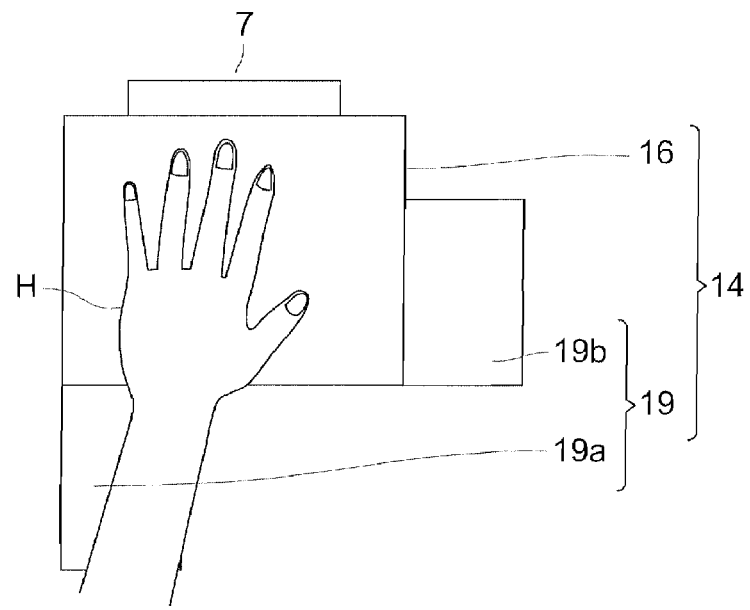
FIG. 11 is a top view showing a variation of a subject table in the invention.
Figure 12:
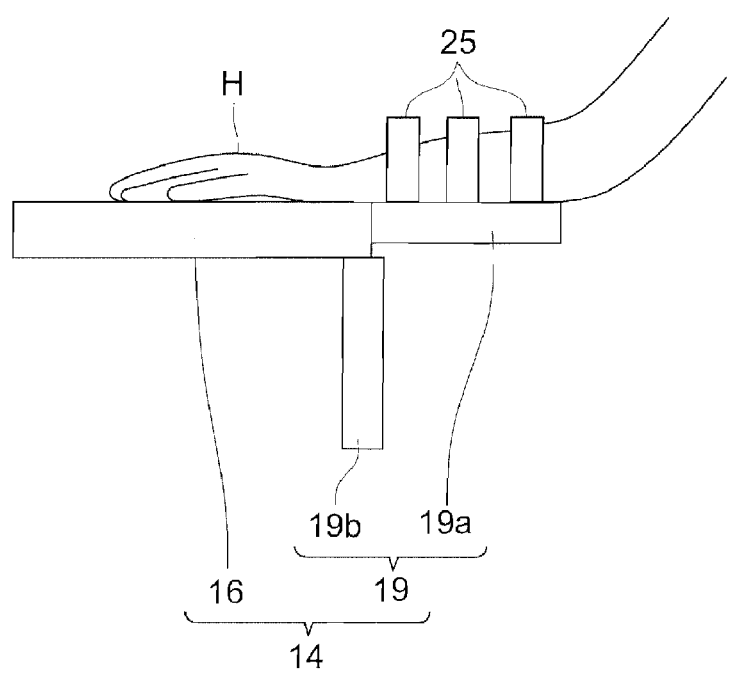
FIG. 12 is a side view showing a variation of a subject table in the invention.
Figure 13:
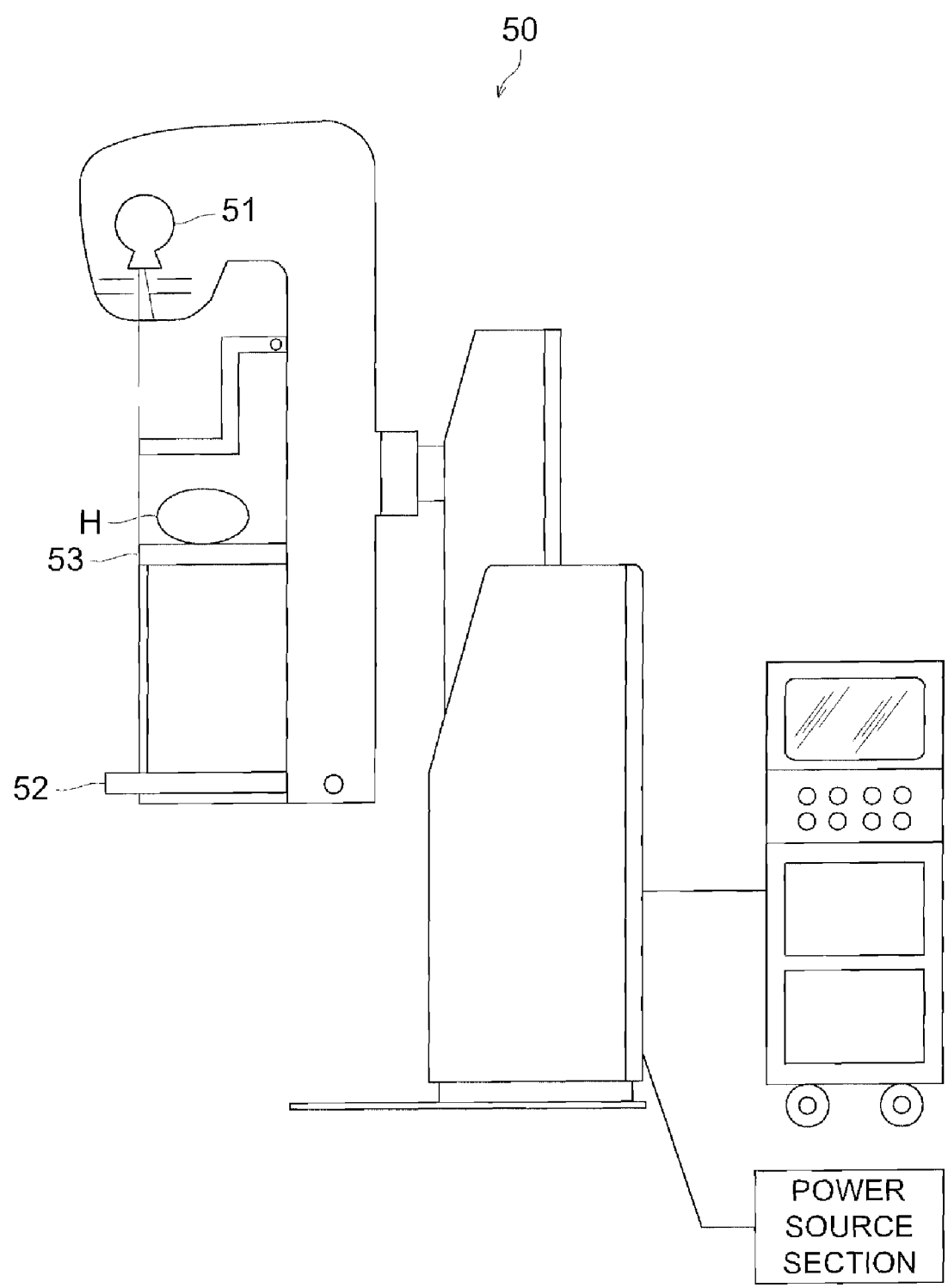
FIG. 13 is a side view showing main structures of a conventional breast image radiographing apparatus.

The arm-holding member 19 has only to be one on which an arm portion of an examinee can be placed, and it can be arranged so that the arm-holding member 19 only is protruded toward the examinee side from the hand-holding member 16 as shown in FIG. 9. In that case, arm-holding member 19 which is not used can be moved in the horizontal direction (see FIG. 10 and FIG. 11) or in the vertical direction (see FIG. 12) to be housed. Further, fixing belt 25 that fixes an arm portion below an elbow of an examinee can also be provided on the arm-holding member 19.

Further, fixing magnets may also be provided between fingers other than the thumb and forefinger on the hand-holding member 16, for fixing fingers of an examinee more firmly. In this case, fingers of the examinee can be fixed without being covered, which does not affect radiographing of joint regions and of bone regions.

In the embodiment of the invention, an examinee can take a comfortable posture by placing its hand and arm portion below an elbow, which makes it easy for an examinee to stay without moving a hand, and makes it possible to radiograph a cartilage region under the circumstances where fingers are fixed. Further, by phase contrast radiographing, circumferential forms of bones and cartilages are edge-emphasized and visibility is vastly improved, which makes it possible to judge presence or absence of aging changes (for example, wearing-off of a cartilage region or the like) of cartilage regions easily and accurately. Since it is further possible to judge presence or absence of aging changes of cartilage regions by using a radiation image photographing apparatus, it is not necessary to use a specific apparatus such as MRI, and it is possible to diagnose a rheumatic disease without placing a burden on the examinee.

In the present embodiment, a height of the apparatus can be made constant, which is preferable from the viewpoint of a building structure for an ordinary clinic and for the department of radiology. It is further possible to adjust the rate of enlargement of phase contrast image to accord with sizes of a radiation image detector and a subject.

In the embodiment of the invention, the hand of an examinee placed on a subject table is judged by a device of discriminating for right and left to be a left hand or a right hand, and a joint region of fingers is radiographed in the prescribed direction, which makes it possible to make an angle of radiographing fingers to be constant, and to judge aging changes easily.

In the embodiment of the invention, the orientation of the hand of an examinee placed on a subject table is judged by a discriminating device for the radiographing direction, and radiation is irradiated in the direction corresponding to the aforesaid orientation for taking an image, which makes it possible to make an angle of radiographing fingers to be constant, and to judge aging changes easily.

In the embodiment of the invention, image data and supplementary information can be made to correspond each other by an information supplementing device and an image data generating section, which takes it possible to conduct observation diagnosis such as comparison with radiation images taken in the past based on supplementary information. Therefore, it is possible to compare with related images (radiation images taken in the past from the same subject) accurately by using supplementary information, even for radiation images of fingers which easily cause mistakes concerning information for right and left and radiographing direction, if they are observed briefly.

What is claimed is:

1. A radiation image photographing system comprising:
    a radiation image photographing apparatus capable of generating a phase contrast image of a finger of an examinee and
    a chair for the examinee to be seated, the apparatus comprising:
        a radiation source for irradiating x-ray radiation to the finger of the examinee sitting on the chair, which is a subject;
        a detector holding device for holding a radiation image detector which detects the x-ray radiation which has been emitted from the radiation source and transmitted through the subject; and
        a subject table for holding the subject, the subject table being located between the radiation source and the detector holding device,
    wherein the subject table comprises:
        a hand-holding member for holding the finger within a range to be radiographed; and
        an arm-holding member which is configured to be capable of placing an arm below an elbow of the examinee thereon in order to fix the finger by resting an arm portion next to the finger thereon, and
    wherein at least the arm-holding member protrudes toward a side of the examinee sitting on the chair, beyond an edge of the detector holding device so that an arm portion next to the finger can rest on the subject table and the finger can be placed stably on the subject table white stabilizing the posture of the examinee by the chair and stabilizing a position of the finer by the subject table.

2. The radiation image photographing apparatus of claim 1, wherein a relative position between the radiation source and the detector holding device is fixed and a relative position of the subject table relative to the radiation source and the detector holding device is changeable.

3. The radiation image photographing apparatus of claim 1, Farther comprising:

a discriminating device for right and left, which discriminates whether the subject held on the subject table is a right hand or a left hand.

4. The radiation image photographing apparatus of claim 3, further comprising:

a discriminating device for a radiographing direction, which discriminates an orientation of the subject held on the subject table.

5. The radiation image photographing apparatus of claim 4, further comprising:

an image data generating section for generating image data of the phase contrast image; and an information supplementing device for attaching at least one of information for right and left created by the discriminating device for right and left and information of a radiographing direction created by the discriminating device for a radiographing direction, to the image data.

6. The radiation image photographing apparatus of claim 1, further comprising:

a discriminating device for a radiographing direction, which discriminates an orientation of the subject held on the subject table.

7. The radiation image photographing apparatus of claim 1, wherein the arm-holding member is configured to protrude from the hand-holding member toward the examinee side.

8. The radiation image photographing apparatus of claim 7, wherein the arm-hoMing member is configured so that the arm-holding member only is protruded toward the examinee side.

9. The radiation image photographing apparatus of claim 7, wherein the arm-holding member comprises a left-arm-holding member and a right-arm-holding member.

10. The radiation image photographing apparatus of claim 9, wherein the arm-holding member is configured so that the left-arm-holding member and the right-arm-holding member separately protrudes from the hand-holding member toward the examinee side.

11. The radiation image photographing apparatus of claim 9, further comprises:

a discriminating device for right and left, which judges whether an arm of the examinee is located on the left-arm-holding member or the right-arm-holding member.

12. The radiation image photographing apparatus of claim 7, wherein the arm-holding member is configured to be movable relative to the hand-holding member.

13. The radiation image photographing apparatus of claim 7, wherein the arm-holding member comprises a fixing belt which fixes an arm portion below an elbow of the examinee.

14. The radiation image photographing apparatus of claim 7, wherein the hand-holding member and the arm-holding member are plate-shaped and thickness of the hand-holding member and thickness of the arm-holding member are different from each other.

15. The radiation image photographing apparatus of claim 14, wherein a surface at a border line between the hand-holding member and the arm-holding member has a step.

16. The radiation image photographing apparatus of claim 7, wherein the hand-holding member and the arm-holding member are plate-shaped and widths of the hand-holding member and the arm-holding member are different from each other, the widths being in a direction perpendicular to a line connecting the range to be radiographed and the examinee sitting on the chair.

17. A radiation image photographing method comprising the steps of:

preparing a radiation image photographing system;

wherein the radiation image photographing system comprises:

a radiation image photographing apparatus capable of generating a phase contrast image and a chair for an examinee to seated, the apparatus comprising:

a radiation source for irradiating x-ray radiation to a finger of the examinee sitting on the chair, which is a subject;

a detector holding device for holding a radiation image detector which detects the x-ray radiation which has been emitted from the radiation source and transmitted through the subject; and a subject table for holding the subject, the subject table being located between the radiation source and the detector holding device, wherein the subject table protrudes toward a side of the examinee sitting on the chair, beyond an edge of the detector holding device so that an arm portion next to the finger can rest on the subject table and the finger can be placed stably on the subject table, while stabilizing the posture of the exaininee by the chair and the subject table, stabilizing the posture of the examinee by the chair and the subject table;

irradiating x-ray radiation to a rheumatism diseased part of a finger joint of the examinee sitting on the chair, which is a subject;

detecting the x-ray radiation which has been emitted from the radiation source and transmitted through the subject, by the radiation image detector; and generating the phase contrast image of the rheumatism diseased part.

* * * * *